(12) United States Patent
Finch et al.

(10) Patent No.: US 7,896,872 A0
(45) Date of Patent: Mar. 1, 2011

(54) APPARATUS FOR THERMAL TREATMENT OF AN INTERVERTEBRAL DISC

(76) Inventors: Philip Michael Finch, South Perth (AU); Eric R. Cosman, Belmont, MA (US)

( * ) Notice: Subject to any disclaimer, the term of this patent is extended or adjusted under 35 U.S.C. 154(b) by 1736 days.

(21) Appl. No.: 09/739,428

(22) Filed: Dec. 18, 2000

(65) Prior Publication Data

US 2004/0015218 A1    Jan. 22, 2004

Related U.S. Application Data

(60) Provisional application No. 60/171,822, filed on Dec. 21, 1999.

(51) Int. Cl.
   *A61B 18/14*    (2006.01)
(52) U.S. Cl. .............. 606/41; 606/27; 607/101
(58) Field of Classification Search ............ 606/41, 606/49, 27–31; 607/108, 109, 115–117, 607/89, 96, 101
See application file for complete search history.

(56) References Cited

U.S. PATENT DOCUMENTS

| | | | |
|---|---|---|---|
| 4,411,266 A | 10/1983 | Cosman | |
| 4,565,200 A | 1/1986 | Cosman | |
| 4,907,589 A | 3/1990 | Cosman | |
| 4,966,597 A | 10/1990 | Cosman | |
| 5,084,043 A * | 1/1992 | Hertzmann et al. | 606/3 |
| 5,122,137 A | 6/1992 | Lennox | |
| 5,315,996 A | 5/1994 | Lundquist | |
| 5,334,145 A | 8/1994 | Lundquist et al. | |
| 5,433,739 A | 7/1995 | Sluijter et al. | |
| 5,437,288 A | 8/1995 | Schwartz et al. | |
| 5,477,856 A | 12/1995 | Lundquist | |
| 5,497,785 A | 3/1996 | Viera | |
| 5,545,193 A | 8/1996 | Fleischman et al. | |
| 5,571,147 A | 11/1996 | Sluijter et al. | |
| 5,573,520 A | 11/1996 | Schwartz et al. | |
| 5,728,149 A | 3/1998 | Laske et al. | |
| 5,833,632 A | 11/1998 | Jacobsen et al. | |
| 5,871,523 A | 2/1999 | Fleischman et al. | |
| 5,951,546 A | 9/1999 | Lorentzen | |
| 5,980,504 A | 11/1999 | Sharkey et al. | |
| 5,983,141 A | 11/1999 | Sluijter et al. | |
| 6,001,093 A | 12/1999 | Swanson et al. | |
| 6,004,279 A | 12/1999 | Crowley et al. | |
| 6,007,570 A | 12/1999 | Sharkey et al. | |
| 6,048,339 A | 4/2000 | Zirps et al. | |
| 6,073,051 A | 6/2000 | Sharkey et al. | |
| 6,095,149 A | 8/2000 | Sharkey et al. | |
| 6,099,514 A | 8/2000 | Sharkey et al. | |
| 6,126,682 A * | 10/2000 | Sharkey et al. | 607/96 |
| 6,146,380 A | 11/2000 | Racz et al. | |
| 6,161,048 A | 12/2000 | Sluijter et al. | |

FOREIGN PATENT DOCUMENTS

| | | |
|---|---|---|
| EP | 0 521 595 B1 | 2/1992 |
| WO | WO93/04722 | 3/1993 |

* cited by examiner

*Primary Examiner* — Roy D. Gibson
*Assistant Examiner* — Aaron Roane

(57) ABSTRACT

An apparatus and method for treating an intervertebral disc having an inner nucleus pulposus and an outer annulus fibrosus includes a thermal probe defining proximal and distal ends and having a guidable region adjacent the distal end thereof. The guidable region is characterized by having sufficient rigidity to advance within the annulus fibrosus of the intervertebral disc in response to an axial force exerted on the proximal end of the thermal probe while having sufficient flexibility to substantially follow and conform to an azimuthal course defined by the natural striata of the annulus fibrosus. The thermal probe is adapted for connection to a thermal energy source to provide thermal energy to the annulus fibrosus to alleviate pain associated with the intervertebral disc.

17 Claims, 3 Drawing Sheets

APPARATUS FOR THERMAL TREATMENT OF AN INTERVERTEBRAL DISC

CROSS REFERENCE TO RELATED APPLICATION

This application is a continuation of provisional application Ser. No. 60/171,822 filed on Dec. 21, 1999.

BACKGROUND

1. Field of the Disclosure

This invention relates generally to advances in medical systems and procedures for prolonging and improving human life. More particularly, this invention relates to a system and method for insertion of a cannula into the intervertebral disc and the insertion of a thermal probe into the disc material to heat the intervertebral disc thereby relieving and treating abnormalities or pain related to the disc.

2. Background of the Disclosure

The use of radiofrequency electrodes for ablation of tissue in the body or for the treatment of pain is known. In a typical situation, a radiofrequency probe or a resistive heating probe commonly constructed in an elongated, cylindrical configuration is inserted into the body to a target tissue which is to be treated or ablated. In the case of a radio frequency probe, there is typically an exposed conductive tip portion and an insulated portion of the probe. When connected to an external source of radiofrequency power, heating of tissue occurs at the exposed conductive portion of the probe, thereby therapeutic changes in the target tissue near the conductive tip are created by the elevation of temperature of the tissue near the tip. Thermal probes can also be made by resistive heating of a portion of the probe so as to heat surrounding tissue by thermal conduction. By reference, the products of Radionics, Inc., located in Burlington, Mass., include radiofrequency generators and electrode systems of varied configurations that are commercially available. A paper by Cosman, et al., entitled "Theoretical Aspects of Radiofrequency Lesions in the Dorsal Root Entry Zone," *Neurosurgery*, December 1984, Vol. 15, No. 6, pp. 945–950, describes aspects of tissue heating using radiofrequency electrodes and probes.

The use of thermal therapy in and around the spinal column is known. Also, the insertion of cannula into the intervertebral discs is commonly done for injection of contrast mediums to implement X-ray discograms. This technique is used to detect or diagnose abnormalities or damage to the intervertebral disc. The use of heating of an intervertebral disc to relieve pain is described in the patent entitled "Method and Apparatus for Heating an Intervertebral Disc for Relief of Back Pain" by Menno E. Sluijter and Eric R. Cosman, U.S. Pat. No. 5,433,739, issued Jul. 18, 1995, and in the patent entitled "Thermal Denervation of an Intervertebral Disc for Relief of Back Pain" by Menno E. Sluijter and Eric R. Cosman, U.S. Pat. No. 5,571,147, issued Nov. 5, 1996. Both U.S. Pat. Nos. 5,433,739 and 5,571,147 are incorporated herein by reference. In these patents, electrodes are described for either radiofrequency or resistive thermal heating of all or a portion of the intervertebral disc. Straight, curved, and flexible-tipped electrodes are described for this purpose. The thermal treatment of an intervertebral disc for the relief of back pain is also described within the patents cited above.

The use of a resistively heated probe adapted to be inserted into the intervertebral disc is described in the product line of the company Oratec Interventions, Inc., located in Menlo Park, Calif. The Oratec instrumentation includes a flexible catheter which is introduced into the nucleus pulposus and manipulated about an inner wall of the annulus fibrosis. A functional element of the catheter treats the nucleus pulposus tissue.

It is desirable to treat the posterior or posterior/lateral portion of the intervertebral disc for the indication of mechanical degeneration of the disc and discogenic back pain. Pain can be derived from degeneration or compression of the intervertebral disc in its posterior or posterior/lateral portions. There is some innervation of the intervertebral disc near the surface of the disc and also within its outer portion known as the annulus fibrosus. Fissures or cracks within the disc caused by age, mechanical trauma, or disc degeneration are believed to be associated with painful symptoms.

Thus, a configuration of insertion cannula to approach and enter the intervertebral disc and a thermal probe to be built into or associated with said cannula to adequately reach the posterior/lateral and posterior portions of the intervertebral disc is desirable. For safety, it is desirable that the surgeon have quantitative information about the placement of the cannula and thermal probe as it is placed in the disc. Risk of the probe kinking within the disc or straying outside of the disc could result in damage to the probe or injury to the patient. A simple and robust cannula and probe system for direct and confirmable placement at the posterior and posterior/lateral portion of the disc is desirable.

SUMMARY

The present disclosure is directed to an apparatus for treating an intervertebral disc having an inner nucleus pulposus and an outer annulus fibrosus. In general, the apparatus includes a thermal probe defining proximal and distal ends and having a guidable region adjacent the distal end thereof. The guidable region is characterized by having sufficient rigidity to advance within the annulus fibrosus of the intervertebral disc in response to an axial force exerted on the proximal end of the thermal probe while having sufficient flexibility to substantially follow and conform to an azimuthal course defined by the natural striata of the annulus fibrosus. The thermal probe is adapted for connection to a thermal energy source to provide thermal energy to the annulus fibrosus to alleviate pain associated with the intervertebral disc. Preferably, the guidable region includes a thermal transmitting element for transmitting thermal energy to the intervertebral disc. The guidable region may include a helical spring.

The apparatus may further include a cannula to facilitate introduction of the thermal probe into the intervertebral disc. The cannula defines a lumen to receive the thermal probe which is advanceable within the lumen. The cannula may include an arcuate end portion which is dimensioned to arrange the guidable region of the thermal probe at a desired orientation within the annulus fibrosus. The cannula may also define a penetrating distal end dimensioned to penetrate the intervertebral disc. Preferably, impedance measuring means are associated with the cannula to monitor the impedance of tissue adjacent a distal end of the cannula to provide an indication relating to tissue condition or type. The impedance measuring means includes a stylet positionable within a lumen of the cannula.

The present disclosure is also directed to a method for relieving pain associated with an intervertebral disc. The method includes the steps of introducing a thermal transmitting element of a thermal probe into the annulus fibrosus of the intervertebral disc and supplying thermal energy from a thermal energy source to the thermal transmitting element to heat the annulus fibrosus adjacent the transmitting element sufficiently to relieve pain associated with the intervertebral disc.

BRIEF DESCRIPTION OF THE DRAWINGS

Further features and advantages of the disclosure will become readily apparent from the following specification and from the drawings, in which.

DESCRIPTION OF PREFERRED EMBODIMENTS

Figure 1:
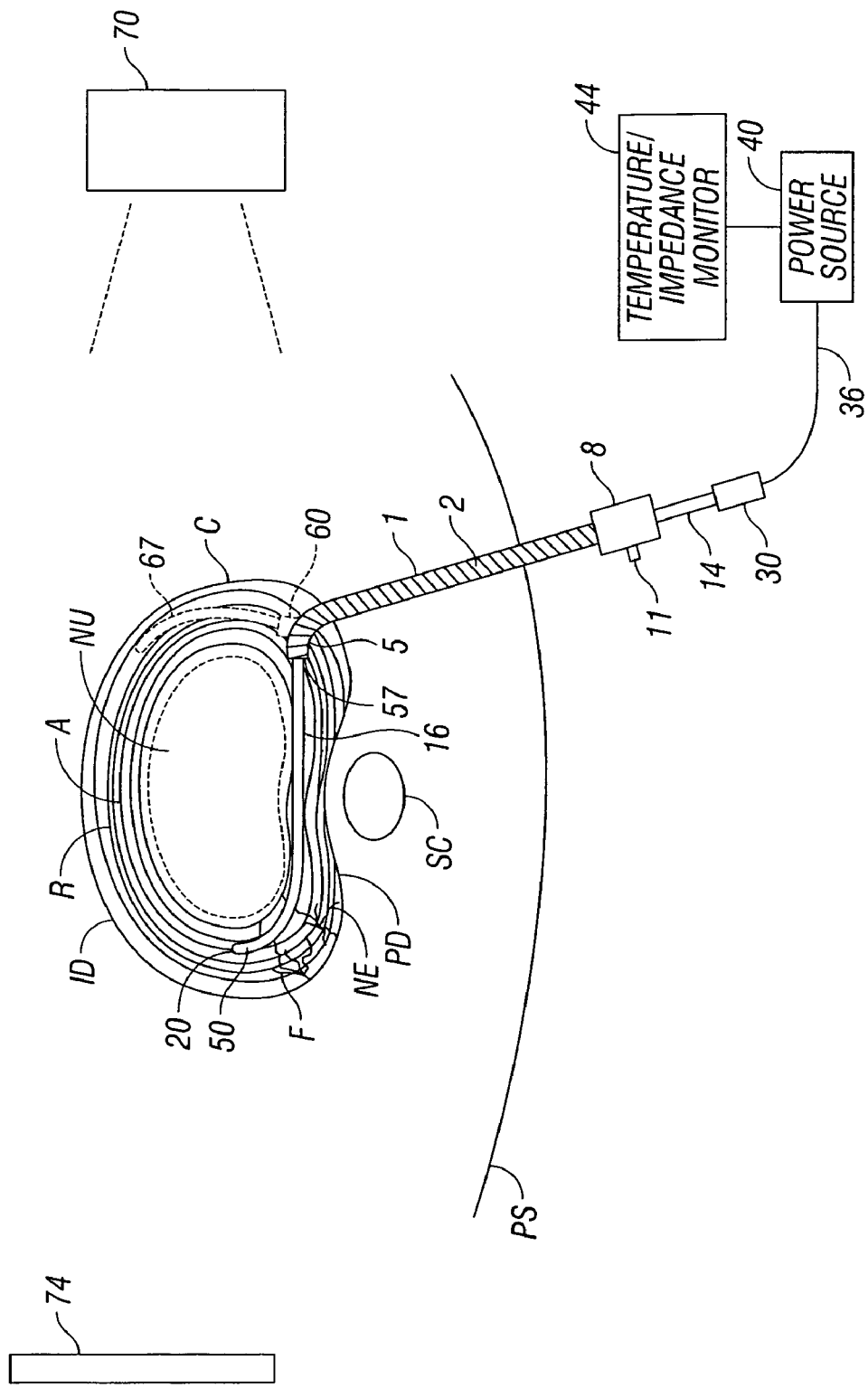
FIG. 1 illustrates the apparatus of the present disclosure inserted percutaneously into an intervertebral disc to thermally treat the disc.

Referring to FIG. 1, the apparatus of the present disclosure introduced into the intervertebral disc is illustrated. Cannula 1 has an insulated portion represented by the hatched area 2 over a portion of its shaft. Cannula has a rigid curved tip portion 5 and a hub 8 with index pin 11 to indicate the direction of the curved portion 5 of the cannula tip. It is inserted manually and percutaneously through the patient's skin PS from the posterior or posterior/lateral position. This is typically done under flouroscopic control. The cannula tip 5 is inserted into the intervertebral disc ID and is placed in the outer annular portion A, referred to as the annulus fibrosus of the disc. The outer annular portion is composed of multiple cartilaginous rings R defining the natural striata of the disc annulus. In the interior of the disc, inside of the dashed line in FIG. 1, is the NU nucleus or nucleus pulposus of the disc, which has a softer consistency than the annulus. The nucleus NU occupies 25–40% of the disc's total cross-sectional area. The nucleus NU usually contains 70–90% water by weight and mechanically functions like an incompressible hydrostatic material. Once the cannula is in place in the outer annulus A, the curved portion of the tip 5 is rotated so as to angulate the tip in a desired direction. Subsequently, a heating probe 14 is inserted into cannula 1. The heating probe has a flexible tip portion 16, which emerges from the distal tip 5 of the cannula 1. The thermal probe tip 16 may have a flexible or semi-flexible nature so that as it emerges from cannula tip 5, it follows along the ringlike course of cartilaginous fibers in the annulus of the disc. As show in FIG. 1, the tip 20 of the thermal probe has reached across the posterior portion PD of the disc and reached the opposite posterior-lateral region of the disc.

The thermal probe 16, as shown in the schematic diagram of FIG. 1, has been positioned directly from a posterior-lateral entry point of cannula tip 5, across the posterior aspect of the disc PD, with its tip in the opposite lateral portion. It is believed that neural innervation occurs significantly in the posterior portion of the annulus A. Such innervation is shown schematically by nerves NE. When mechanical stress is put upon a disc or a disc degenerates with patient age, fissures, illustrated by the cracks F, also occur in the posterior or posterior/lateral portions of the disc. The placement of the electrode, as shown in FIG. 1, locates the thermal tip 16 in the region where the nerves NE and the fissures F often occur. Problems with the nerves and fissures and degenerative discs can give rise to various patient problems such as back pain originating from the irritation or occurrence of these abnormalities. Heating of the disc and its annulus in the posterior or posterior-lateral portions will result in alterations and thermal ablation of these structures, which will in turn produce alleviation of pain and healing of the disc. Thus, it is desirable, as shown in FIG. 1, to have a practical method of placing a thermal probe in the posterior and/or posterior-lateral portion of a disc where these neural and aberrant structures occur for the relief of pain and other disc related problems.

The cannula 1 and/or electrode 16 is shown in FIG. 1 connecting by connector cable 36 to an external power source 40. The connection 36 is shown in FIG. 1 to couple through hub 30 and connect onto shaft portion 14, which connects in turn to thermal probe 16. The external power source 40 may be a source of high frequency current, voltage, power, an ultrasonic source, a source of laser or electromagnetic energy, or a resistive power heating source. By reference, high frequency generators that produce heating on electrodes are illustrated by the model RFG-3C Lesion Generator System from Radionics, Inc., Burlington, Mass. The power source 40 may have control devices to increase or modulate power output as well as readout and display devices to monitor energy parameters such as voltage, current, power, frequency, impedance, and so forth. Also shown in FIG. 1, in connection with the power source, is a temperature or impedance controlling or monitoring device 44. This may, for example, monitor the impedance of tissue through the electrode 16 in the tissue or through the cannula 1 via an exposed portion of the cannula as it contacts the tissue during insertion or during the heating process. The heat probe 16 may have a thermal sensor, illustrated by element 50, at one or more points in its configuration. The temperature, as read out by such temperature sensors 50, can be determined and monitored by element 44.

The cannula 1, in accordance with one exemplary embodiment, may comprise a rigid tubular shaft made of metal such as stainless steel or other compositions. It may be sufficiently rigid to pierce tissue. Its curved tip portion comprises a rigid, curved portion which may have various angular orientations, radius of curvature, and length of curved potion to suit clinical needs. The insulation portion 2 may be of common insulation materials. By reference, electrode shafts and insulation materials are illustrated by the electrodes produced by Radionics, Inc., Burlington, Mass. The distal portion 57 of cannula 1 may have an open face with a pointed or semi-pointed tip. There may be an exposed metal portion near or at the tip 57 or curved portion 5, which enables electrical connection to or contact with the tissue as the cannula is placed in the body. During the insertion phase, therefore, impedance of the tissue near the tip may be measured from the exposed conductive tip by monitor 44, thereby determining tissue interfaces as the cannula and/or electrode is advanced first into the tissue, then into the cortex C of the disc, the annulus A of the disc, and farther on into the nucleus NU of the disc.

By way of one specific example, the power source 40 may be a radiofrequency generator with frequency between several kilohertz to several hundred megahertz. An example of such a generator is the lesion generator available from Radionics, Inc., Burlington, Mass. It may have a power output range from several watts to several hundred watts, depending on clinical need. The cannula 1 may be a circular stainless steel or other alloy metal tube with diameters ranging from a fraction of a millimeter to several millimeters. It may have a length of a few centimeters up to 10, 15, 20, or more centimeters.

Insertion of cannula 1 may take place initially through the patient's skin PS and directed towards the intervertebral disc ID, as illustrated in FIG. 1. In one instance, the curved probe 5 may be directed as shown by the solid line drawing to project the thermal probe 16 so that its tip 20 moves toward the opposite portion of the disc. In another orientation, illustrated by the dashed line tip 60, the shaft of the cannula 1 is rotated to another angle so that the thermal probe, illustrated by the dashed line 67, is extending from the tip of the cannula to the ipsilateral portion or some side of the disc. This is illustrated by the dotted line 67, representing the position of the thermal probe in this angular orientation of the cannula tip 60. It is, therefore, an advantage of the present invention in the embodiment shown in FIG. 1 that the curved portion of the cannula 1 can be used to angulate and direct the thermal probe in a variety of directions, depending on the azimuthal angular position of the shaft 1 and its angle of direction into the disc ID, cortex C, annulus A, and nucleus NU.

Direction of the cannula 1 and thermal probe 16 can be monitored, controlled, and/or quality assured by imaging systems of various kinds. FIG. 1 illustrates an imaging device 70 in proximity to the patient's body. This may, for example, be an X-ray machine, a flouroscopic machine, or an ultrasonic, CT, MRI, PET, or other imaging device. Some of these devices have conjugate elements, as illustrated by element 74, on the opposite portion of the patient's body to provide imaging data. For example, if image 70 is an X-ray machine, element 74 may be a detection device such as an X-ray film, digital, X-ray detector, flouroscopic device, etc. Use of imaging machines to place percutaneously placed electrodes into the disc or regions around the disc is practiced in pain relief in other surgical interventions.

Figure 2:
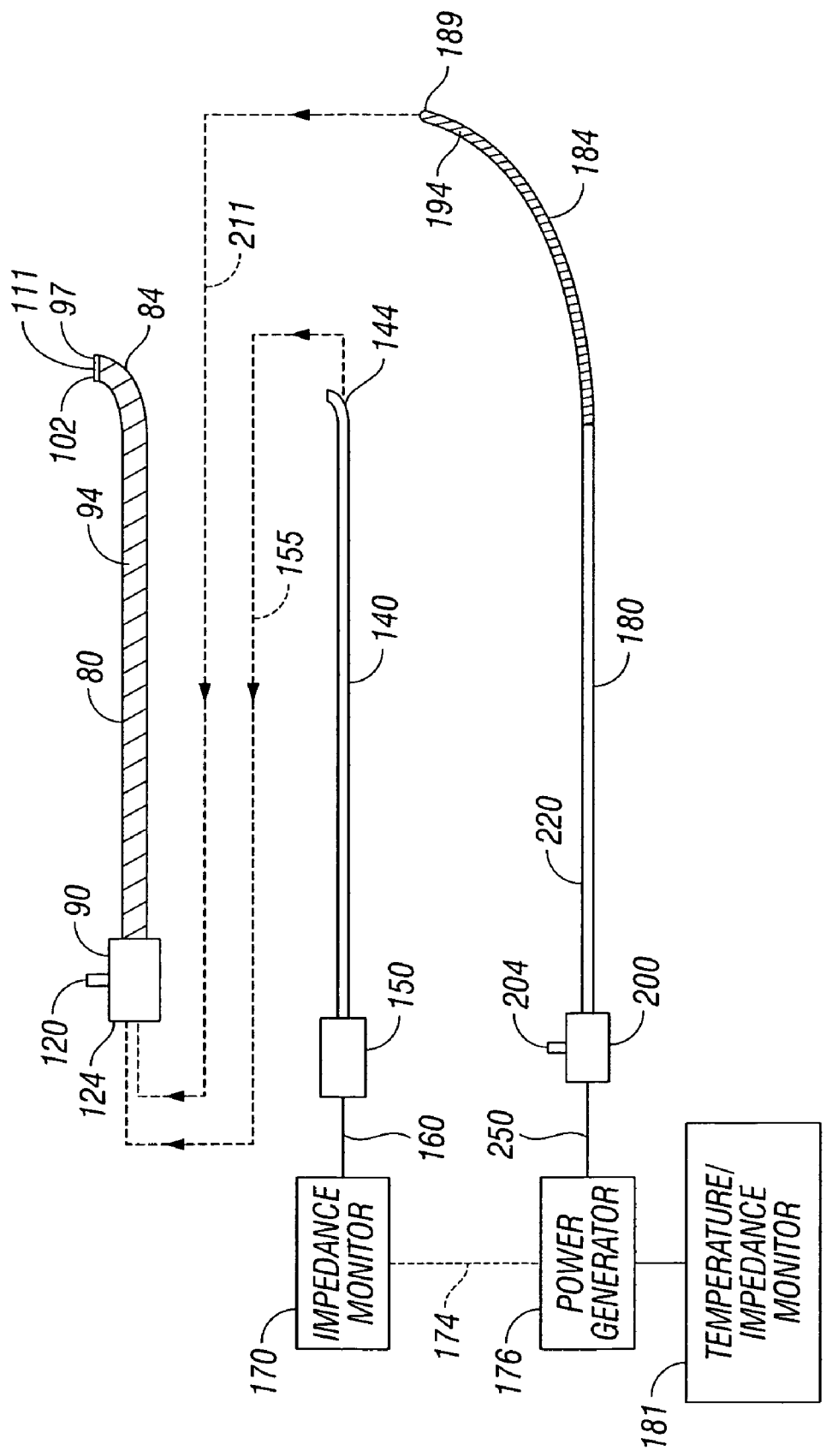
FIG. 2 illustrates in side plan view the apparatus of FIG. 1 disassembled to depict the outer cannula, an obturating stylet for insertion into the cannula and a thermal probe with flexible and/or steerable tip portion for insertion into the cannula.

Referring to FIG. 2, side view representations or embodiments of the cannula, stylet, and thermal probe devices with connections to external agents are shown in accordance with the present invention. Cannula 80 may have a rigid shaft, a curved distal portion 84, and a proximal hub 90. It can be insulated over a portion of substantially all of its surface area, as illustrated by the hatched area 94. This insulation may be of various kinds, as illustrated by Teflon, polyurethane, or other standard coatings. The tip portion 97 may have a pointed structure and an open portion 102. Also shown is an uninsulated segment 111, which may illustrate an uninsulated, exposed, or conductive portion of the metal shaft 80 at the distal end of the cannula. This may be used as a stimulating, impedance monitoring, or micro-thermal generating tip. For example, if the cannula is comprised of a metal tube, insulation 94 may cover most of the tubing, except for an exposed, uninsulated portion 111 at the distal tip. This portion 111 may be of a relatively small area and be connected to an external impedance monitor 170 to monitor the impedance of tissue as the electrode is advanced into the patient's body and the intervertebral disc region. Hub 90 may be a plastic or metal hub or be made of other compositions to facilitate gripping the electrode and pushing it into the patient's body. Index marker 120 may indicate the direction of the curved portion 84 at the cannula's distal tip so that when the electrode is placed into the body, the surgeon can determine in which azimuthal rotation direction the curve is directed. The hub may have an opening 124 on its proximal end that may have a cylindrical, luer taper, or other shape.

Also shown is a stylet 140, which may be a metal shaft or non-metal shaft with a curved distal portion 144. The distal portion may be permanently curved or it may be flexible to follow the curve of the cannula's rigid curved end 84. The stylet may have a hub 150 that is shaped to mate to the hub 124 of cannula 80. In FIG. 2 it is shown in one embodiment with a connection means 160 that connects the stylet to external monitor apparatus 170, for example, to measure impedance as the cannula and stylet are being inserted into the intervertebral disc. Other connections 174 may connect the stylet and therefore the cannula 80 to power generators 176 to other parameter monitors 181 (viz. temperature, impedance, current, voltage, power, or other relevant heating or monitoring outputs).

The stylet 140 may be used in conjunction with the cannula 80 when the cannula is being inserted into the patient's body. Dashed line 155 illustrates that the stylet 140 can be inserted into the cannula 80. The stylet 40 may occlude the front opening 111 of the cannula and the hub 150 may mate to the hub 120 to lock the two structures together during insertion. An impedance monitor 170 can be connected, as shown by connection 160, to the stylet and therefore communicate electrically with the exposed portion 111 of the cannula into which the stylet is introduced. Alternatively, connection of the impedance monitor may be made directly to the shaft of cannula 80. Once the combination of stylet and cannula are inserted into the body, impedance monitoring may determine the position of the cannula tip 97 with respect to the patient's skin PS, the cortex C of the disc, the annulus A, and/or nucleus NU of the disc ID. These regions will have different impedance levels that can be thereby detected.

Also shown as part of the system in accordance with the present invention in FIG. 2 is the thermal probe 180 with flexible distal portion 184 and distal tip 189. It has a hub portion 200 with direction index pin 204 to indicate the direction of curvature of the distal portion 184. When the stylet 140 is removed from the cannula, the thermal probe may be inserted into the cannula 80, as illustrated by the dashed line 211. The degree of extension of the tip portion 184 beyond the opening 102 of the cannula may be indicated by distance markings 220 on the shaft of the thermal probe 180.

The construction of the cannula can be made in different configurations and materials. The shaft 80 can be made of rigid tubing such as stainless steel or from various other materials which, for example, can be MRI compatible. MRI compatible materials made of cobalt alloys, titanium, copper, nitinol, etc. are examples. The insulation can take various forms and thickness. The tubing diameter may be in the range of a fraction of a millimeter to several millimeters. The length of the shaft 80 may be from a few centimeters to many centimeters. The hub 90 can be of plastic or metal for various degrees of radiopacity or translucency. The dimensions of the uninsulated portion 111 can vary from a fraction of a millimeter to several millimeters, or even centimeters, depending on clinical needs. The degree of curvature and radius of curvature and configuration of the curvature of the distal tip 84 can vary widely in geometry depending on clinical needs.

Stylet 140 can be made of a rigid metal tubing with either a permanent bend 144 or a straight but flexible material to adapt to the curve of the cannula 80 when it is inserted within the cannula. The hub 150 and connector 160 can take various forms including luer hubs, plug-in-jack-type connections, integral cables, etc. By reference, example of electrodes and cables are illustrated in the product lines of Radionics, Inc., Burlington, Mass.

The thermal probe in FIG. 2 can have variations in construction and geometry in accordance with the present invention. For example, the shaft 180 can be made from a metal tube, a wire structure, or a helix of wire. It can be fully insulated, partially insulated, or not insulated at all, depending on construction needs. The distal portion 184 can be a floppy helical spring or a more rigid bent structure with some memory of its shape. It can be a more springy structure with a permanent curve, depending on the needs of stiffness, floppiness, curvature to accommodate differing disc structures. In one exemplary embodiment, the distal portion 189 can be a helical, flexible, exposed metal electrode that has appropriate flexibility to follow the path of the disc annulus or nucleus to accommodate positioning in the posterior, posterior-lateral, anterior, or anterior-lateral configuration of the disc, annulus, or nucleus, as illustrated, for example, in FIG. 1 above. The tip portion 189 may have a slight curvature so as to produce steering of the electrode when it is pushed into the disc material or the azimuthal striations (e.g., cartilaginous rings) of fibers within the annulus A, as shown in FIG. 1. Within the distal portion may be thermal sensors, as illustrated by the position 194 in FIG. 2. The thermal sensors can be connected by internal wires through the hub 200 and further through a connection cable 250 to external apparatus such as the power generator 176 or temperature or impedance monitors 181.

In another configuration of the thermal probe in FIG. 2; the probe 180 and 184 may include resistive heating elements and connections so that the distal end 184 heats up by resistive heating of a thermal element within 184. For example, within the distal end 184 there may be a resistive wire such as a nichrome wire or other type of resistive element, such that current delivered to the resistive element from the power generator 176 will produce resistive heating within the element. Such heating of the proximate disc material when the electrode is inserted into the disc of a patient. Various construction details for such resistive heating elements 184 can be devised by those skilled in the art. For example, a helical resistive wire can be fabricated to produce the structure 184 with a particular curvature. Alternatively, an internal resistive wire can be placed inside of a helical spring or other structure. The overall shaft 180 and 184 may be coated with an insulative material or other material to produce appropriate frictional, thermal, or electrical characteristics of the electrode when it is placed in the disc. Like the high frequency electrode embodiment, as described above, such a resistive element 184 may have the appropriate flexibility, pre-curve, or steering capability so that it can be steered or directed favorably within the appropriate portion of the posterior and posterior-lateral portions of a disc, as illustrated by the discussion associated with FIG. 1 above.

In another configuration of the thermal probe, as shown in FIG. 1 in accordance with the present disclosure, the distal end may comprise a microwave antenna system or a laser fiber with transducer to distribute energy through thermal element 184 into surrounding disc tissue. In the configuration shown in FIG. 1, the thermal transmitting element operates as a microwave antenna or laser transmitting element, respectively. Other constructions to produce a heating element 184 can be devised by those skilled in the art and are intended to be included within the scope of the present invention.

Figure 3:
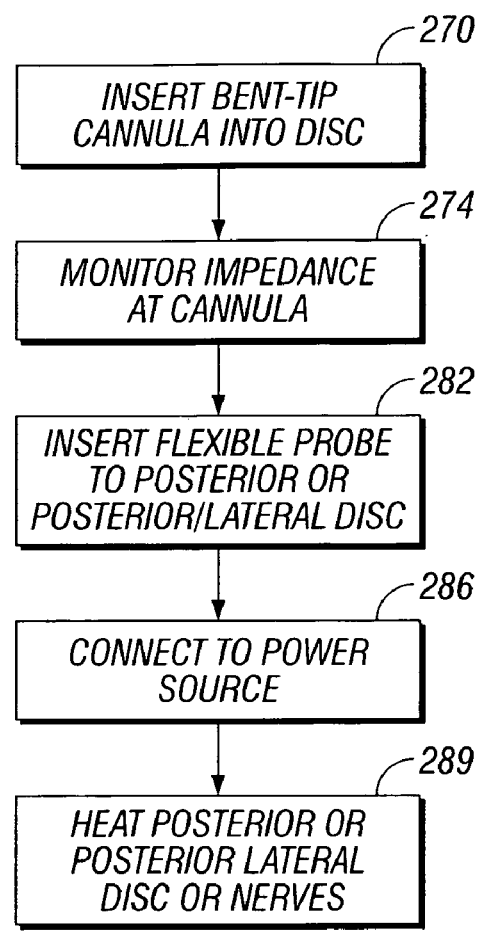
FIG. 3 illustrates a flow chart of the operation of the apparatus.

FIG. 3 illustrates the steps of a procedure in accordance with the present invention. A bent tip cannula of the appropriate configuration is selected for insertion into the patient's body towards an intervertebral disc which is to be treated by thermal therapy (step 270 in FIG. 3). The electrode of appropriate curvature and tip exposure may be selected for various disc positions ranging over the cervical, thoracic, lumbar, and sacral regions. Different geometries of cannula may differ depending on which disc site is to be treated. Monitoring the impedance from the catheter or from a stylet that is within the catheter to detect changes in the impedance as the tip is inserted through the skin, through the underlying tissue, through the cortex C of the disc, into the annular structure A of the disc, or into the nucleus NU of the disc (step 274 in FIG. 3). The impedance of these different anatomical tissue sites, varies significantly enough that changes of impedance, as represented by the impedance monitor in the external apparatus, can indicate to the surgeon the position and depth of the cannula on its course into the appropriate location within the disc. For example, for a fully insulated electrode with an exposed area of a few square millimeters cannula end, the impedance will change significantly from the position of the tip near to or contacting the cortex C of the disc to the region where the tip is within the annulus A of FIG. 1 and further where the tip of the disc is within the nucleus NU of the disc, as shown in FIG. 1. Differences of impedance can range from a few hundred ohms outside the disc, to 200 to 300 ohms in the annulus, to approximately 100 to 200 ohms in the nucleus. This variation can be detected exquisitely by the surgeon by visualizing impedance on meters or by hearing an audio tone whose frequency is proportional to impedance. Such a tone can be generated by monitor 181 in FIG. 2. In this way, an independent means is provided in step 274 in accordance with this invention of detecting placement of the curved cannula within the disc.

Once the cannula is appropriately placed within the disc ID, the stylet may be withdrawn from the cannula and the thermal probe inserted into the cannula such that the thermal probe disc is introduced into the intervertebral disc (step 282 in FIG. 3). The curved cannula may be directed in various positions and/or rotations, as illustrated in FIG. 1. The thermal probe with its flexible tip can then be pushed out of the open end of the cannula into the annulus or the nucleus of the disc. Because of its flexible, steerable, and/or bent/curved configuration, the probe tip can be pushed along a path defined by the natural striata the appropriate point within the disc, where atrophy, degeneration, injury, or innervation of the disc is believed to be the site of the patient's symptoms. As illustrated in FIG. 1, the probe can be extended by a few millimeters to several centimeters beyond the tip end of the cannula into remote portions of the disc. The thermal probe can be passed from the right posterior-lateral portion of the disc where the cannula is located to the left posterior and/or posterior-lateral, or even the anterior and/or anterior-lateral portion of the disc. The thermal probe can be made to pass around and indeed wrap around the configuration of the disc through the natural striata or lamina of the annulus A or nucleus NU, as illustrated in FIG. 1.

Once the thermal probe is properly placed, it can be connected to the external power source (step 286). If the external power source is a high frequency, radiofrequency, microwave, DC current, AC current, laser power, or ultrasonic power source, this connection will enable energy to emanate from the thermal probe tip into the disc tissue to produce the thermal therapy in accordance with the present invention. Appropriate amounts of power, current, thermal heat, or light energy may be monitored from the external power source and delivered to the disc for a certain amount of time as determined appropriate for clinical needs (step 289). When the amount of heating and time duration of heating is determined to be appropriate, the thermal probe can be withdrawn back into the cannula and the entire system removed from the patient's body.

It is a significant advantage of the present system that a curved cannula can be introduced into the disc for thermal therapy. Accordingly, it is an advantage, in accordance with the present invention, that a cannula can be placed in the posterior or posterior-lateral portion of the disc and a thermal probe can be directed from that point across the posterior margin and into the contralateral posterior-lateral portion of the disc by a direct pathway along, e.g., the natural striata of the annulus fibrosis A. This represents a more direct approach to the posterior/lateral portions of the disc than a more circuital approach involving delivering a probe into the center of the disc and then arcing the probe around through an anterior or anterior-lateral pathway.

A further advantage of the present invention is that by monitoring impedance of the cannula and/or the thermal probe as its is being positioned within the disc, the surgeon can get additional information on the positioning of the cannula as it is being put into the proper orientation. Furthermore, monitoring of impedance of the cannula and the thermal probe before, during, or after the thermal treatment give an indication of the degree of desiccation, power rise, boiling or charring, that may be taking place near the electrode. This indicates the effectiveness of the treatment and guards against untoward or unsafe contraindications of the therapy. By reference, use of impedance monitoring in neurosurgery is described in the paper by E. R. Cosman and B. J. Cosman entitled "Methods of Making Nervous System Lesions", in *Neurosurgery*, Vol. 3, pp. 2490–2499, edited by R. H. Wilkins and S. S. Rengachary, McGraw-Hill, 1985. A further advantage of the present invention is that by use of a curved introduction cannula a more efficacious direction of the electrode can be achieved in the difficult lumbar or lumbar-sacral intervertebral discs. In these approaches, nearby heavy bony structures, such as the iliac crest, can often obscure a placement of a curved probe parallel to the end plates or bony margins of adjacent intervertebral discs. By appropriate angulation and rotation of a curved cannula, the extension of a thermal probe parallel to the so-called end plates of the intervertebral discs is made possible with minimal repositioning and manipulation of the introduction cannula.

In typical radiofrequency procedures using the apparatus and process of the present invention, power levels of fractions of a watt to several tens of watts may be used depending on the extent of heating required and the degree of therapy, innervation, and disc healing that is desired to be achieved.

A further advantage of the present system and method is that it enables simple, minimally-invasive, percutaneous, outpatient treatment of interdiscal pain without the need for open surgery as for example discectomies or spinal stabilization using plates, screws, and other instrumentation hardware. A further advantage of the present system is that it is simple to use and relatively economical. Compared to open surgery, the treatment of disc by percutaneous electrode placement represents only a few hours procedure and minimal hospitalization, with minimal morbidity to the patient. Open surgical procedures often require full anesthetic, extensive operating room time, and long hospital and home convalescence. Such open surgeries have considerable risk of morbidity and mortality and are much more expensive than a percutaneous procedure as described in accordance with the present invention.

What is claimed is:

1. A method for relieving pain associated with an intervertebral disc having a nucleus pulposus and an annulus fibrosus surrounding the nucleus pulposus, comprising the steps of:

introducing a thermal transmitting element of a thermal probe into the annulus fibrosus of the intervertebral disc, the thermal probe defining proximal and distal ends and having a guidable region adjacent the distal end thereof the guidable region characterized by having sufficient rigidity to advance within the annulus fibrosus of the intervertebral disc in response to an axial force exerted on the proximal end of the thermal probe while having sufficient flexibility to substantially follow and conform to an azimuthal course defined by the natural striata of the annulus fibrosus;

advancing the thermal transmitting element of the thermal probe within the annulus fibrosus while avoiding the nucleus pulposus; and supplying thermal energy from a thermal energy source to the thermal transmitting element to heat the annulus fibrosus adjacent the transmitting element while avoiding directly heating the nucleus pulposus sufficiently to relieve pain associated with the intervertebral disc.

2. The method according to claim 1 wherein the thermal probe includes a flexible probe portion, whereby the flexible probe portion follows a generally arcuate path within the annulus fibrosus.

3. The method according to claim 2 wherein the step of advancing the thermal transmitting element of the thermal probe includes passing the flexible probe portion generally along an arcuate path defined by natural striata of the annulus fibrosus.

4. The method according to claim 1 wherein the step of advancing includes positioning the thermal transmitting element adjacent at least one of a posterior section, lateral section and posterior-lateral section of the annulus fibrosus.

5. The method according to claim 4, including the step of accessing the annulus fibrosus from a posterior-lateral section of the intervertebral disc.

6. The method according to claim 1 further including the step of positioning a cannula adjacent the intervertebral disc and passing the thermal probe through a lumen of the cannula into the annulus fibrosus.

7. The method according to claim 6 wherein the cannula includes an arcuate portion adjacent a distal end thereof and wherein, during the step of advancing the thermal probe, the arcuate cannula portion guides the flexible probe portion along the path through the the annulus fibrosus.

8. The method according to claim 7 wherein the step of positioning includes at least partially introducing the distal end of the cannula into the annulus fibrosus.

9. The method according to claim 8 further including the step of angulating the arcuate portion to a desired orientation within the annulus fibrosus.

10. The method according to claim 1 further including the step of monitoring impedance of tissue to detect variations in tissue-type to thereby facilitate positioning of the thermal transmitting element in the annulus fibrosus.

11. The method according to claim 1 further including the step of monitoring the position of at least the thermal transmitting element with imaging means.

12. A method for relieving pain associated with an intervertebral disc, the intervertebral disc having a disc nucleus and an annulus fibrosus surrounding the disc nucleus, the method comprising the steps of:

accessing an intervertebral disc with a cannula;

advancing a thermal probe having a heat transmitting region through the cannula into the intervertebral disc and within the annulus fibrosus while avoiding the disc nucleus to, position the heat transmitting region of the thermal probe in at least one of posterior, lateral and posterior-lateral areas of the annulus fibrosus, the thermal probe defining proximal and distal ends and having a guidable region adjacent the distal end thereof, the guidable region characterized by having sufficient rigidity to advance within the annulus fibrosus of the intervertebral disc in response to an axial force exerted on the proximal end of the thermal probe while having sufficient flexibility to substantially follow and conform to an azimuthal course defined by the natural striata of the annulus fibrosus; and supplying thermal energy from a thermal energy source to the heat transmitting region to heat the annulus fibrosus while avoiding directly heating the disc nucleus to treat pain associated with the intervertebral disc.

13. The method according to claim 12 wherein the step of accessing includes advancing a distal end of the cannula through the intervertebral disc to position the distal end within the annulus fibrosus.

14. The method according to claim 13 wherein the cannula includes an arcuate portion adjacent the distal end thereof and further including the step of manipulating the arcuate portion to a desired orientation with respect to the annulus fibrosus.

15. The method according to claim 14 wherein the heat transmitting region of the thermal probe is substantially flexible and wherein during the step of advancing, the heat transmitting region bends within the arcuate portion of the cannula.

16. The method according to claim 13 wherein the cannula includes impedance means and wherein the step of accessing includes monitoring impedance of tissue to ascertain a location of the distal end of the cannula in relation to the intervertebral disc.

17. The method according to claim 16 wherein the step of monitoring impedance of tissue further includes monitoring a plurality of impedance interfaces including the tissue and a cortex of the intervertebral disc, the cortex and the annulus fibrosus of the intervertebral disc, and the annulus fibrosus and the disc nucleus of the intervertebral disc.

* * * * *